US006165452A

United States Patent [19]

[11] Patent Number: 6,165,452
[45] Date of Patent: Dec. 26, 2000

Boden et al.

[54] CYCLIC TRIMERS OF ALDEHYDES, ORGANOLETPIC USES THEREOF AND PROCESS FOR PREPARING SAME

[75] Inventors: Richard M. Boden, Ocean; William L. Schreiber, Freehold, both of N.J.; Freddy Tabak, Hilversum; Henricus Gerardus Maria Reijmer, Hoevelaken, both of Netherlands

[73] Assignee: International Flavors & Frangrances Inc., New York, N.Y.

[21] Appl. No.: 09/358,000

[22] Filed: Jul. 21, 1999

[51] Int. Cl.[7] .............................. A61K 7/32; A61K 7/00; A61K 7/46

[52] U.S. Cl. ........................... 424/65; 424/400; 424/401; 512/1; 512/8; 512/25

[58] Field of Search ................................... 424/400, 401, 424/65; 512/1, 8, 25

[56] References Cited

U.S. PATENT DOCUMENTS 4,330,474 5/1982 Nehring ................................. 549/367

FOREIGN PATENT DOCUMENTS 905115 3/1999 European Pat. Off. .
9734578 9/1997 WIPO .

*Primary Examiner*—Shelley A. Dodson
*Assistant Examiner*—Marina Lamm
*Attorney, Agent, or Firm*—Arthur L. Liberman

[57] ABSTRACT

Described are novel aldehyde cyclic trimers which are useful for controllably releasing fragrance composition components into the environment surrounding the location of said trimers. The trimers are particularly useful in effecting malodor elimination from solid or semisolid surfaces, e.g., the human epidermis (skin) and surfaces that have a displeasing tobacco aroma.

8 Claims, No Drawings

CYCLIC TRIMERS OF ALDEHYDES, ORGANOLETPIC USES THEREOF AND PROCESS FOR PREPARING SAME

BACKGROUND OF THE INVENTION

The present invention relates to novel compositions of matter suitable as long lasting fragrances, particularly insofar as the fragrances are used in long lasting underarm deodorants or antiperspirants or are used for long lasting malodor coverage compositions. The present invention concerns the use of specific ingredients for effecting such control release as opposed to the use of entrapped fragrances within, for example, matrices. Such ingredients are novel products of reaction of (i) aldehydes with alcohols; (ii) ketones with alcohols; and (iii) aldehydes with the same or other aldehydes.

It is well known in the prior art to utilize entrapped fragrances which are controllably releasable from matrices in order to provide malodor coverage and deodorancy. Furthermore, it is well known in the prior art to use certain non-reacted mixtures of materials in order to cover malodors, e.g., NEUTRIFF®, trademark of International Flavors & Fragrances Inc., a mixture of GALAXOLIDE® (trademark of International Flavors & Fragrances Inc.), corn mint oil and citral.

Furthermore, Procter & Gamble Company PCT Published Application No. 94/28107 discloses a perfume delivery system useful, for example, in granular detergent compositions for covering the malodor thereof and providing a new aroma therefor comprising:

(a) a solid, water-soluble porous carrier which comprises a natural or synthetic zeolite having a nominal four sides of at least six angstroms;

(b) a perfume which is releasably incorporated in the pores of the zeolite carrier to provide a perfumed zeolite preferably comprising 5–30 weight percent of the perfume; and (c) a matrix coated on the perfumed zeolite which comprises a water-soluble composition in which the perfume is substantially insoluble.

The matrix of PCT Published Application No. 94/28107 coated on the perfume zeolite comprises a water-soluble composition in which the perfume is substantially insoluble. The matrix comprises 0–80 weight percent of at least one solid polyol containing more than three hydroxyl moieties; and 20–100 weight percent of a fluid diol or polyol in which the perfume is substantially insoluble and in which the solid polyol is substantially soluble. It is indicated in PCT Published Application No. 94/28107 that the perfume delivery composition is useful in detergent compositions, for example, a granular detergent composition comprising 5–80 weight percent detergent surfactant and 1–20 weight percent of the perfume delivery composition. The composition of PCT Published Application No. 94/28107 is indicated to provide a perfume delivery system which provides odor benefits during and after the laundry process, but which has reduced product odor during storage. It is further indicated that after removal of the matrix in the wash, the system provides the additional benefit of continued odor release when exposed to heat or humidity while being stored, dried or ironed.

U.S. Pat. No. 4,428,869 issued on Jan. 31, 1984 (Munteanu, et al), incorporated by reference herein, describes hydro-alcohol compositions of matter, including but not limited to colognes, after-shave lotions, after-bath preparations and splash lotions which yield continuously high fragrance intensity release, evenly and uniformly over an extended period of time and which can be adapted to yield differing aromas from a qualitative and quantitative standpoint in a controllable manner containing a mixture of (i) a non-confined fragrance composition; (ii) one or more fragrance oils which are physically entrapped in one or more types of solid particles; and (iii) a suspending agent such as hydroxypropyl cellulose, silica, xanthan gum, ethyl cellulose or combinations of the previously-mentioned four substances; the non-confined fragrance substance, the entrapped fragrance oil and the suspension agent being premixed prior to the subsequent creation of the hydro-alcohol composition of matter.

However, nothing in the prior art, including the above-mentioned references, discloses the use as a control release material, particularly for deodorization properties of a fragrance composition of matter which contains pre-reacted (i) aldehydes with alcohols; (ii) ketones with alcohols; and (iii) aldehydes with the same or other aldehydes.

However, the use of acetals in perfumery and otherwise for the effect of said acetals on organoleptic properties of the products in which they are placed is well known in the prior art. Thus, Japanese Published Patent Application (Kokai) No. 110/29517 (Kuraray Company, Ltd.) published on Jul. 10, 1997 indicates that certain acetals are useful as synthetic "starting material for perfumes . . . . " More specifically, Kuraray Company, Ltd., Japanese Published Patent Application No. 110/29517, states that acetals having the structures:

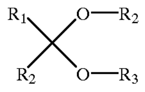

and

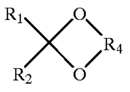

produced according to the reaction of aldehydes or ketones of the formula:

$$R_1R_2C{=}O$$

with alcohols of the formula: $R_3OH$ or of the formula: $HOR_4OH$ in the presence of a nickel complex catalyst of the formula:

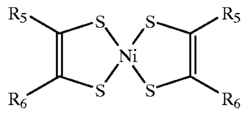

(wherein $R_1$ and $R_2$ may be hydrogen or substituted or unsubstituted $C_1$–$C_{20}$ monovalent hydrocarbon; or $R_1$ and $R_2$ may be bonded to one another; and $R_3$ is substituted or unsubstituted $C_1$–$C_{20}$ monovalent hydrocarbon; and $R_4$ is alkenylene, optionally having an ether bond; and $R_5$ and $R_6$ are substituted or unsubstituted saturated hydrocarbon or substituted or unsubstituted aromatic hydrocarbon) are useful as synthetic starting materials for perfumes. In addition, Korea Ginseng & Tobacco Research Institute, Korean Patent No. 98/009214 filed on Jul. 16, 1996 discloses pyruvaldehyde dimenthyl acetal and preparation thereof.

However, nothing in the prior art discloses explicitly or implicitly the novel products of reaction of (i) aldehydes with alcohols; (ii) ketones with alcohols; and (iii) aldehydes with the same or other aldehydes, particularly the use thereof for controllably releasing fragrance compositions and/or fragrance composition components into the environment surrounding the location of such products of reaction. Furthermore, nothing in the prior art discloses that the above-said products of reaction are particularly useful in effecting malodor elimination from solid or semisolid surfaces, e.g., skin (the human epidermis) or surfaces that have a displeasing tobacco aroma.

THE INVENTION

Our invention concerns novel products of reaction of (i) aldehydes with alcohols; (ii) ketones with alcohols; and (iii) aldehydes with the same or other aldehydes.

More specifically, our invention concerns products of reaction of aldehydes with alcohols and ketones with alcohols forming acetals, hemiacetals, ketals and hemiketals having the generic structures:

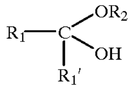

(hemiketals and hemiacetals); and

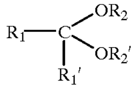

(acetals and ketals), produced by means of the reaction of the alcohol having the structure: $R_2$—OH or the structure: $R_2'$—OH with the ketone or aldehyde having the structure:

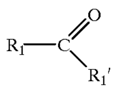

according to the reactions:

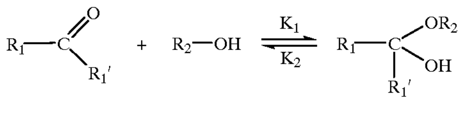

or

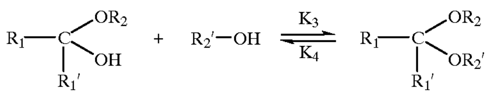

wherein the terms $k_1$, $k_2$, $k_3$ and $k_4$ are reaction rate constants and wherein the terms $R_1$, $R_1'$, $R_2$ and $R_2'$ define moieties resulting from the reactions of the following aldehydes and ketones:

hexylcinnamic aldehyde;
LILIAL®;
heliotropine;
LYRAL®;
AUBEPINE™;
undecylenic aldehyde;
dodecanal;
hedione;
methyl ionone; and
ISOCYCLEMONE E® with the following carbinols:

citronellol;
nerol;
geraniol;
dihydromyrcenol;
β-phenyl ethyl alcohol;
tetrahydrolinalool;
ROSALVA®; and
undecavertol.

Our invention is also directed to novel cyclic triacetals produced by means of trimerization of aldehydes, dimerization of aldehydes or reaction of different aldehydes with one another. Such products have the structure:

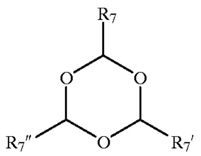

produced according to the reactions:

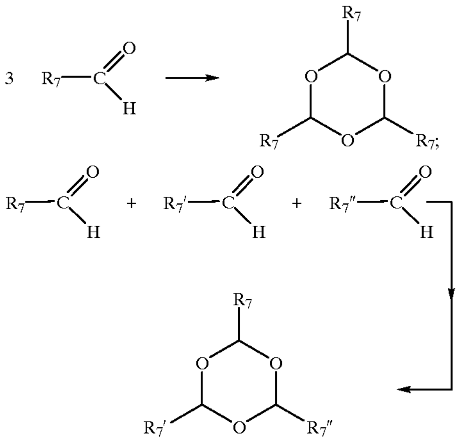

; and wherein $R_7$, $R_7'$, $R_7''$, are moieties created as a result of the reaction of the following aldehydes with one another and with themselves:

heliotropine;
undecylenic aldehyde;
LILIAL®; and
AUBEPINE™.

By the term LILIAL® (trademark of Givaudan-Roure of Basel, Switzerland) is meant the compound having the structure:

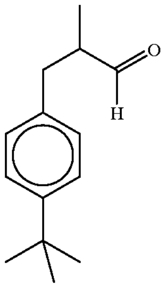

By the term "AUBEPINE™" is meant the compound having the structure:

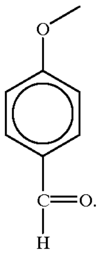

By the term "ROSALVA® (trademark of International Flavors & Fragrances Inc.) is meant the compound having the structure:

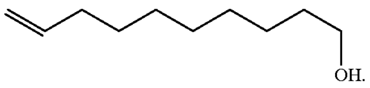

By the term "LYRAL®" (trademark of International Flavors & Fragrances Inc.) is meant the mixture of compounds defined according to the structure:

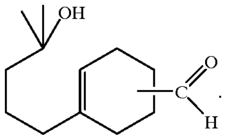

By the term "hexylcinnamic aldehyde" is meant the compound having the structure:

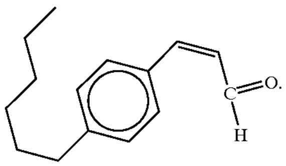

By the term "nerol" is meant the compound having the structure:

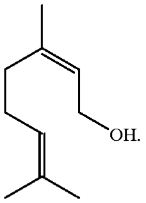

By the term "ISOCYCLEMONE E®" is meant the compound having the structure:

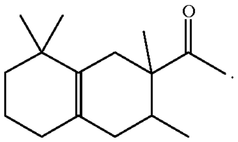

Thus, for example, when "AUBEPINE™" is trimerized, it forms the compound having the structure:

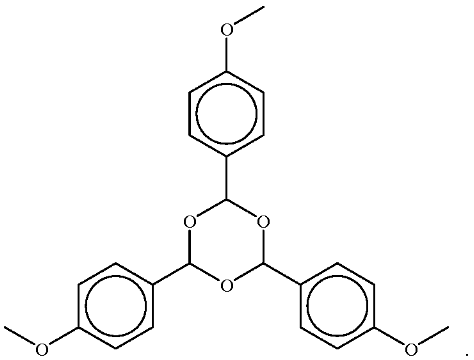

On the other hand, when ISOCYCLEMONE E® is intended to be reacted with ROSALVA®, it is first reacted with 2 moles of methyl alcohol to form the dimethyl ketal having the structure:

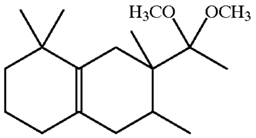

after which the dimethyl ketal is reacted with the ROSALVA® in accordance with the following reactions:

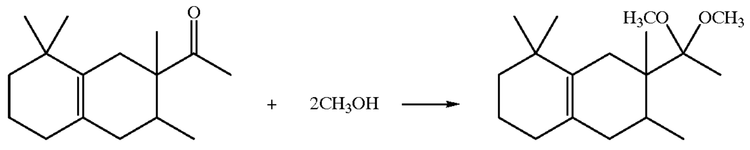

; and

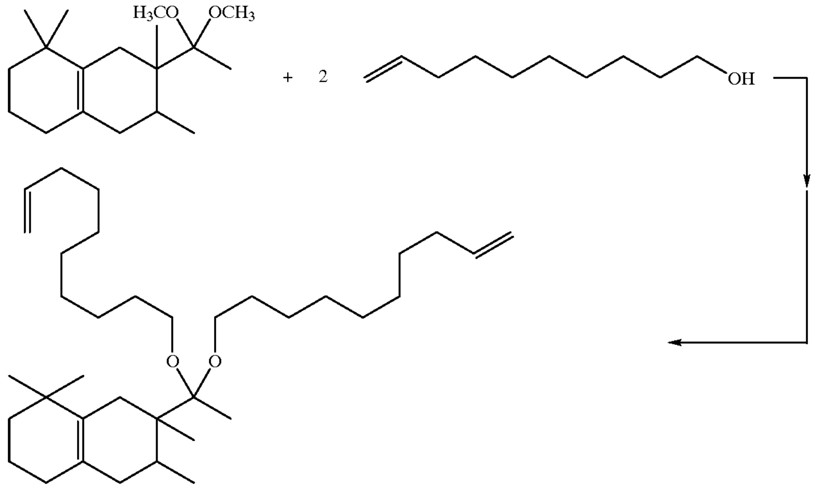

By the same token, when "LYRAL®" is reacted with geraniol, the digeranyl acetal of LYRAL® is formed, a mixture of compounds according to the reaction:

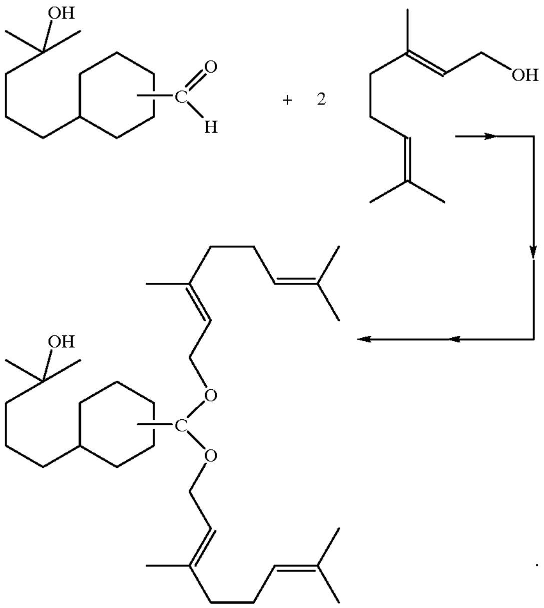

.

When a mixture of geraniol and ROSALVA® are reacted with AUBEPINE™, the "mixed" acetal having the structure:

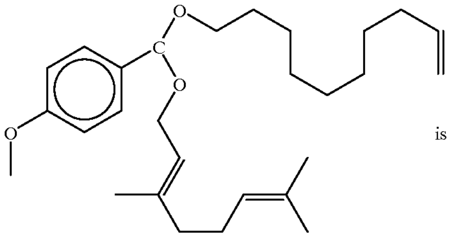

is formed.

An example of a "mixed" trimer of AUBEPINE™ and heliotropine has the structure:

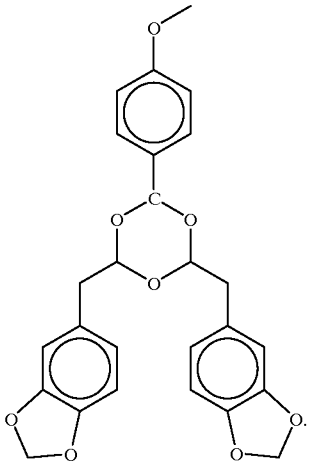

.

Of key importance is the rate at which the reaction products of our invention decompose in order to form the constituent aldehydes, ketones and alcohols of our invention, which are in and of themselves, taken alone or in admixture, fragrance components or fragrance compositions. Thus, the reactions:

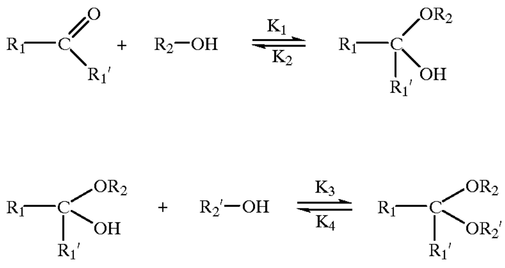

may be shown thusly:

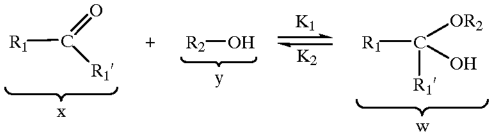

and

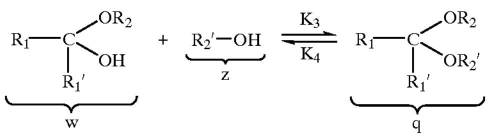

wherein the symbol “x” is for the concentration in the reaction mass of the ketone having the structure:

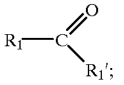

the symbol “y” is the concentration in the reaction mass of the alcohol having the structure:

$R_2$—OH;

the symbol “w” is the concentration in the reaction mass of the hemiacetal or hemiketal having the structure:

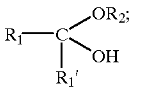

the symbol “z” is for the concentration in the reaction mass of the alcohol having the structure:

$R_2'$—OH; and the symbol “q” is for the concentration in the reaction mass of the acetal or ketal having the structure:

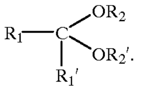

Thus, when the hemiacetals and ketals are being formed, for example, when the reactions of the alcohols and the aldehydes take place in the presence of an acid catalyst such as citric acid, the rates of formation of the hemiacetals, hemiketals, acetals and ketals are in accordance with the equations:

$$\frac{dw}{d\theta} = k_1[x][y] - k_2[w] = -\frac{dx}{d\theta} \text{ and}$$

$$\frac{dQ}{d\theta} = k_3[w][z] - k_4[Q] = -\frac{dw}{d\theta}$$

wherein the term $$\frac{dw}{d\theta}$$

is the rate of formation of the hemiacetal or hemiketal; the symbol $$-\frac{dx}{d\theta}$$

is the rate of disappearance of the ketone or aldehyde; the symbol $$\frac{dQ}{d\theta}$$

is the rate of formation of the acetal or ketal; and the symbol $$-\frac{dw}{d\theta}$$

is the rate of disappearance of the hemiacetal.

When the resultant acetals or ketals are then decomposed, for example, when they are placed in a basic medium or even neutral medium and exposed to air, the oxidation/reduction half reactions take place, to wit:

$4e^- + O_2 + 2H_2O \rightarrow 4OH$ and

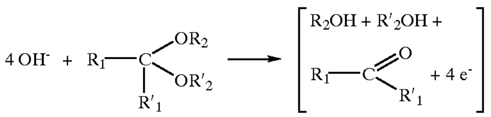

and the kinetics of the decomposition is shown by the following equations:

$$\frac{dx}{d\theta} = \frac{dy}{d\theta} = k_2[w]; \quad \frac{d^2x}{d\theta^2} = k_2\left[\frac{dw}{d\theta}\right];$$

$$\frac{dw}{d\theta} = \frac{dz}{d\theta} = k_4[Q]; \quad \frac{1}{k_2}\left[\frac{d^2x}{d\theta^2}\right] = \frac{dw}{d\theta} = k_4[Q]; \text{ and}$$

$$[Q] = \frac{1}{k_2k_4}\left[\frac{d^2x}{d\theta^2}\right] = \frac{1}{k_2k_4}\left[\frac{d^2y}{d\theta^2}\right].$$

The terms of these equations are as follows:

the term:

$$\frac{dx}{d\theta}$$

is the rate of formation of the ketone or aldehyde;

the term:

$$\frac{dy}{d\theta}$$

is the rate of formation of the alcohol having the structure:

$R_2$—OH;

the term:

$$\frac{d^2x}{d\theta^2}$$

is the rate of change with respect to time of the rate of formation of the aldehyde or ketone;

the term:

$$\frac{dz}{d\theta}$$

is the rate of formation of the alcohol having the structure:

$R_2'$—OH;

the term:

$$\frac{dw}{d\theta}$$

is the rate of formation of the hemiacetal or hemiketal having the structure:

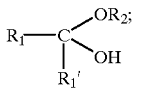

the term:

$$\frac{d^2y}{d\theta^2}$$

is the rate of change with respect to time of rate of formation of the alcohol having the structure: $R_2$—OH; and the term: θ is for the time of the reactions in general. Furthermore, as the acetal or ketal is formed in the presence of the acid catalyst, e.g., citric acid, the concentration of the acetal or ketal is a function of the reaction rate constants $k_1$, $k_2$, $k_3$ and $k_4$ as well as the concentrations in the reaction mass of each of the other components, thusly:

$$[Q] = \frac{k_1[x][y] - k_2[w] + k_3[w][z]}{k_4}.$$

As the acetal or ketal decomposes to its constituent aldehydes, ketones and alcohols on the solid or semisolid surface (e.g., human epidermis), the concentration of acetal or ketal having the structure:

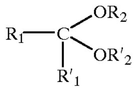

changes over the period of time Δθ according to the equations:

$$\frac{1}{k_4} ln \frac{Q_2}{Q_1} = \left[\frac{1}{k_{EQ[II]}}\right]\Delta\theta - k_2\Delta\theta;$$

$$\frac{Q_2}{Q_1} = \left\{e^{\left[\frac{k_4}{k_{EQ[II]}}\right]\Delta\theta - k_2\Delta\theta}\right\}; \text{ and}$$

$$Q_2 = Q_1\left\{e^{\left[\frac{k_4}{k_{EQ[II]}}\right]\Delta\theta - k_2\Delta\theta}\right\},$$

wherein $k_{EQ[II]}$ is the equilibrium constant for the reaction:

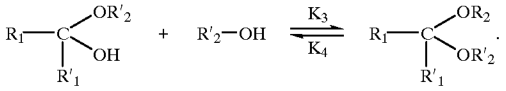

The following examples are illustrative and the invention is not to be restricted except as indicated by the appended claims.

EXAMPLE I

The following two mixtures were prepared:

(i) 50% diethyl phthalate and 50% hexylcinnamic aldehyde; and (ii) 50% dihydromyrcenol, 50% hexylcinnamic aldehyde and a trace of citric acid.

Each mixture is stirred for a period of 72 hours. At the end of the 72-hour period, each mixture is sprayed onto cloth odorized with "stale tobacco aroma."

The cloth treated with composition (ii) had the "stale tobacco aroma" completely removed and/or covered and the cloth had a pleasant, floral aroma.

On the other hand, the cloth sprayed with composition (i) retained the "stale tobacco aroma."

EXAMPLE II

The following formulation is prepared:

| Ingredients | Parts by Weight |
|---|---|
| citric acid powdered anhydrous | 1.00 |
| citronellol coeur | 30.00 |
| dihydromyrcenol | 50.00 |
| geraniol | 25.00 |
| hexylcinnamic aldehyde | 100.00 |
| LILIAL ® | 50.00 |
| LYRAL ® | 30.00 |
| ROSALVA ® | 5.00 |
| tetrahydrolinalool | 100.00 |
| undecavertol | 3.00 |

This material is termed: Formulation "A."

The second formulation was then prepared, Formulation "B":

| Ingredients | Parts by Weight |
|---|---|
| citronellol coeur | 30.00 |
| dihydromyrcenol | 50.00 |
| hexylcinnamic aldehyde | 100.00 |
| LILIAL ® | 50.00 |
| LYRAL ® | 30.00 |
| ROSALVA ® | 5.00 |
| tetrahydrolinalool | 100.00 |
| undecavertol | 3.00 |

Formulation A and formulation B were then stirred for a period of 72 hours. At the end of the 72 hours, each of formulations A and B were placed into 100 ml pump dispensers.

10 Grams of each of the formulations were sprayed evenly onto tea towels. Prior to being used, the tea towels had been washed at high temperature (95° C.) in unfragranced detergent powder in order to ensure that there was no surface contamination. The sprayed tea towels were then left for 72 hours in exactly similar storage conditions. After 72 hours, the tea towels were assessed in terms of strength alone by a 30-member panel.

The tea towels sprayed with formulation A had an aroma intensity scaled at "10" on a scale of 1–10 as assessed by a 30-member panel. The tea towels sprayed with formulation B had a value of "5" for intensity as assessed by the 30-member panel.

The tea towels sprayed with formulation A had a pleasant aroma which lasted for a period of 144 hours at the same level as assessed by the 30-member panel. The tea towels sprayed with formulation B, after 144, hours had an aroma scaled at "1" by the 30-member panel.

In conclusion, the acetal-containing formulation A is far superior for both substantivity and strength to the non-reacted components.

EXAMPLE III

Preparation of Deodorancy Stick

A wax-type deodorant stick formulation having the following composition is prepared by mixing ingredients and parts by weight:

| Ingredients | Parts by Weight |
|---|---|
| ARISTOWAX ® 165 (registered trademark of Witco Chemical Corporation for parraffin wax) | 14.0 |
| ozokerite wax 170-D (hydrocarbon wax) | 8.0 |
| white petrolatum | 13.0 |
| ACETULAN ® (acetylated lanolin alcohol manufactured by Amerchol Chemical Company) | 2.8 |
| di-isopropyl adipate | 6.0 |
| mineral oil | 52.1 |
| propyl paraffin | 0.1 |
| ketal produced by reacting 50 parts of ISOCYCLEMONE E ® (registered trademark of International Flavors & Fragrances Inc.) with 50 parts by weight of ROSALVA ® (trademark of International Flavors & Fragrances Inc.) in the presence of 0.1% citric acid | 12.0 |

The resulting composition is heated to 75° C. until melted. The resulting suspension is then poured into stick molds, thereby formulating deodorant sticks containing fragrance therein, each stick being cylindrical and having a length of 3 inches and a diameter of 1 inch.

A similar product is produced with the exception that the ISOCYCLEMONE E® and ROSALVA® are placed in the formulation separately, without pre-reacting them.

A panel test is conducted on 30 independent panelists to demonstrate which product produced has the strongest fragrance after 8 hours. Of the 30 panel members, 30 panelists (100%) perceived the fragrance produced from the composition containing the pre-reacted ROSALVA® and ISOCYCLEMONE E® (in the presence of citric acid) as being 5 times as strong as the material produced containing the individual ingredients: ROSALVA® and ISOCYCLEMONE E®, not being pre-reacted.

What is claimed is:

1. A process for controllably releasing fragrances onto a solid or semisolid surface originally emitting a malodorous substance, comprising the step of applying to said solid or said semisolid surface a malodor-removing quantity and concentration at a malodor-removing rate of a composition of matter consisting essentially of at least one cyclic triacetal of at least one aldehyde selected from the group consisting of:

(a) the compound having the structure:

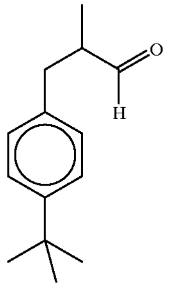

(b) heliotropine;

(c) the compound having the structure:

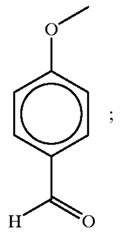
;

(d) undecylenic aldehyde;

(e) dodecanal; and (f) the mixture of compounds defined according to the structure:

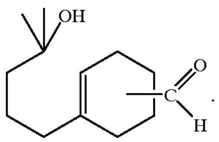
.

2. A product produced according to the process of claim 1.

3. The process of claim 1 wherein the product produced thereby is admixed with a deodorant stick base and the resulting mixture is formulated into a deodorant stick.

4. The process of claim 1 wherein the product produced thereby is admixed with an antiperspirant stick base and the resulting mixture is formulated into an antiperspirant stick.

5. The product produced according to the process of claim 3.

6. The product produced according to the process of claim 4.

7. A composition of matter consisting essentially of at least one cyclic triacetal of an aldehyde selected from the group consisting of:

(a) the compound having the structure:

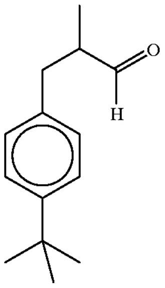
;

(b) heliotropine;

(c) the compound having the structure:

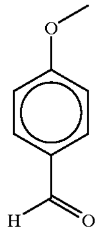
;

(d) undecylenic aldehyde; and (e) a mixture of compounds defined according to the structure:

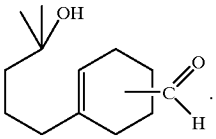
.

8. The composition of claim 7 having the structure:

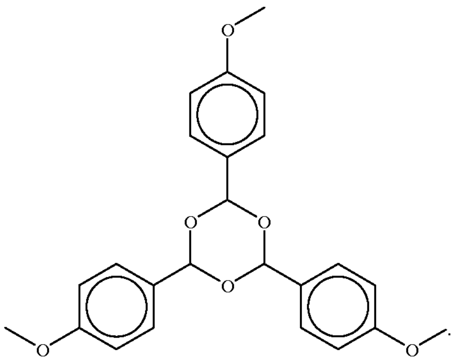
.

* * * * *